United States Patent [19]

Maurel et al.

[11] Patent Number: 6,129,924
[45] Date of Patent: Oct. 10, 2000

[54] DIGLYCERIDE AND STEROL BASED ORGANOMETALLIC COMPLEXES AND PHARMACEUTICAL COMPOSITIONS AND DIETETIC PRODUCTS CONTAINING THEM

[75] Inventors: Jean-Claude Maurel, Castries; Jean-Marc Chapuis, Puteaux; Jean-Jacques Mongold, Juvignac; Nicolas Jouy, Montpellier, all of France

[73] Assignee: Maurel Sante, Castries, France

[21] Appl. No.: 08/945,761

[22] PCT Filed: Jun. 30, 1997

[86] PCT No.: PCT/FR97/01153

§ 371 Date: Jul. 13, 1998

§ 102(e) Date: Jul. 13, 1998

[87] PCT Pub. No.: WO98/01461

PCT Pub. Date: Jan. 15, 1998

[30] Foreign Application Priority Data

Jul. 3, 1996 [FR] France ................................. 96 08263

[51] Int. Cl.[7] .......................... A61K 31/28; A61K 31/29; A61K 31/295; A61K 31/315
[52] U.S. Cl. ...................... 424/400; 424/195.1; 424/617; 424/618; 424/630; 424/639; 424/641; 424/646; 424/649; 424/650; 424/651; 424/682; 514/169; 514/866
[58] Field of Search ................................ 424/400, 195.1, 424/617, 618, 630, 639, 641, 646, 649, 650, 651, 682; 514/169, 866

[56] References Cited

FOREIGN PATENT DOCUMENTS

| 2686511 | 7/1993 | France . |
| 2686512 | 7/1993 | France . |
| 2686514 | 7/1993 | France . |
| 3686515 | 7/1993 | France . |

OTHER PUBLICATIONS

Chemical Abstracts #187365 vol. 116, No. 19, May 1992.
Chemical abstract #580. vol. 121 #1, Jul. 1994.
Chemical Abstract #34320. vol. 116 #5, Feb. 1992.
Chemical Abstracts #442. vol. 103 #1, Jul. 1985.
Chemical Abstract #069237 vol. 110 #9, Feb. 1989.

*Primary Examiner*—Gollamudi S. Kishore
*Attorney, Agent, or Firm*—Dennison, Scheiner Schultz & Wakeman

[57] ABSTRACT

The invention relates to an organometallic complex obtainable by reaction:

- of a cation of a metal (M) in an oxidation state at least equal to 2 useful as a biocatalyst in living metabolism,
- of a mixture of sitosterol and sitostanol, or of pure sitostanol or of a plant extract containing same,
- of the diglyceride of formula (I):

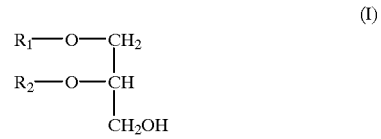

in which:

$R_1$ is an acyl residue of oleic acid ($C_{18}$:1),

R2 in an acyl residue of a linear or branched, saturated or unsaturated fatty acid having between 2 and 18 carbon atoms. More particularly, the invention relates to complexes in which $R_2$ is an oleoyl or acetyl group. The invention also relates to pharmaceutical compositions containing this complex, particularly those wherein the metal is vanadium, and to their use in the treatment and/or the prevention of hypercholesterolaemia and/or of hypertriglyceridaemia, of insulin-dependent or non insulin-dependent diabetes, of insulin resistance and associated pathologies.

24 Claims, No Drawings

DIGLYCERIDE AND STEROL BASED ORGANOMETALLIC COMPLEXES AND PHARMACEUTICAL COMPOSITIONS AND DIETETIC PRODUCTS CONTAINING THEM

This application is a 371 of PCT/FR97/01153 filed Jun. 30, 1997.

BACKGROUND OF THE INVENTION

The present invention relates to organometallic complexes based on sterols and diglycerides as novel industrial products.

The invention also relates to pharmaceutical compositions and dietary products containing these complexes.

Acylglycerols, more particularly acylglycerols of fatty acids, are present in the majority of plants and are the main constituents of plant and animal fats.

The only variations from one acylglycerol to another is the number of fatty acids, their position on the glycerol, their chain length and the number and the position of the unsaturated bonds they may contain. In particular, these are mono-, di-, or triacylglycerols.

For both sitosterol and sitostanol, there exists two active isomers, the β-and the γ-isomer. These are also constituents of all plants. In the text, the term sitosterol comprises the beta or the gamma sitosterol (or a mixture of these two isomers), and the term sitostanol comprises beta or gamma sitostanol (or a mixture of these two isomers).

Certain total extracts of plants which, like the majority of plants, contain amongst their very many constituents flavonoids, tannins, saponins, coumarins, alkaloids, triterpenes, sterols, carbohydrates and/or glycosides have been described for their hypoglycaemic activity, such as, for example, acacia extract (Egypt. J. Pharm. Sci., 1992, 33 (1–2), 327–340), or Teucrium oliveranium extract (Fitoterapia, 1984, 55(4), 227–230). No link between the activity and the fraction containing the sterols is established. In these publications, this activity is generally attributed to carbohydrates or polyols of cyclohexane such as condutirol, An inositol derivative isolated from a Gymnema sylvestra extract which does not reduce glycaemia directly, but prevents the sugars from passing through the wall of the intestine.

Some sapogenins have been described for the treatment of diabetes, (sarsasapogenin and similagenin for example, in EP 0 204 661). These are derivatives whose lateral chain is constituted of two cyclic spiro ethers.

Other hypoglycaemic derivatives of plant origin have been described, such as, for example:
 the glycoside of leucopelargonidin in Indian J. Exp. Biol. 1993, 31(1), 26–29;
 the glycosides of prototimosaponin in Chemical Abstracts 117(9):83451f which is a summary of the Japanese patent JP 04054194;
 ginsenoside Rb2 described in Chemical Abstracts 105(17) :146237r which is a summary of the Japanese patent JP 61024597. This product tested on the rat acts as an antidiabetic, the dose via the intraperitoneal route being 10 mg/per rat. This dose reduces the glycaemia by 20%.

The leaves and flowering extremities of the nettle (*Urtica dioica*) are known traditionally for their antidiabetic properties (first description in the scientific literature was 1926). This activity is reproducible and quantifiable, but nobody has hitherto isolated the active principle(s).

Plant sterols, particularly those from the root of the nettle (*Urtica dioica*) have for many years been the subject of many studies, especially for the treatment of certain tumors such as adenoma of the prostate.

A *Pygeum africanum* plant extract, marketed in France for many years by Laboratoires DEBAT under the trademark of TADENAN® for the treatment of adenoma of the prostate, has been the subject of recent studies which tend to prove that the activity would be due to the sterol-lipid fraction which contain, according to R. Longo and S. Tyra, Farmaco, Ed. Pract. 1983, 38(7), pages 287–292, beta-sitosterol, beta-sitosteryl glucoside and 3 beta-sitostenone as well as n-docosanol and n-docosyl trans-ferulate, according to Chemical Abstracts CA 104(22): 193255j.

In Journal of Natural Products, 1987, 50(5), pages 881–885, N. Chaurasia and M. Wichtl describe the isolation, the separation, and the identification of certain sterols from the root of the nettle.

In 1979, a team of Brazilian researchers described, in Rev. Med. Univ. Fed. Ceara, 19(1–2), 49–53, a green arabica coffee bean extract of which sitosterol would be hypoglycaemic. Since then, it has not been possible for this activity to be reproduced and no work has been published which confirms it.

U.S. Pat. No. 4,588,717 describes, as vitamin supplement, weight reducer and diet supplement which reduces the absorption of carbohydrates, and therefore glycaemia, a mixture containing metals, metal complexes and fructose, vitamins, fatty acids, phospholipids, esters of sterols, amino-acids, etc.

The authors of this patent do not describe as such the therapeutic activity, they do not attribute the properties of their mixture to any one family of products present in the mixture.

The hypocholesterolaemic virtues of plant sterols have been known for several decades. They reduce cholesterolaemia by inhibiting the intestinal absorption of cholesterol (by co-precipitation or by displacement of the bonds between the micelles). The addition to the diet of large quantities of these sterols, sitosterol in particular, at a daily dose of at least 30 g has been used since the fifties for the treatment of hypercholesterolaemia, but the unpleasant taste and texture of these preparations has been an obstacle to its use. Such activity can only be obtained with large amounts of sitosterol.

Miettinen et al.( New England Journal of Medicine, 1995, vol. 333, n°20, p.1308) have developed a margarine containing an ester of sitostanol. According to these authors, sitostanol greatly reduces the absorption of cholesterol by the intestine. A double blind study was carried out for one year on a population suffering from moderate hypercholesterolaemia. 51 subjects consumed a margarine enriched in sitostanol ester (2.6 g /day). After one year, a reduction of 10% of the total cholesterolaemia and a reduction of 14% in the LDL was observed in these patients. No change in the level of triglycerides nor of HDL was observed. It must be noted however that the study was carried out on a population having a high intake of cholesterol, and the authors doubt that a comparable activity would be observed in subjects whose diet is low in cholesterol, since sitostanol is not absorbed and its activity is confined to the inhibition of the absorption of cholesterol by the intestine.

A hypocholesterolaemic activity has also been described in the animal: Antihypercholesterolaemic activity in rabbits: I. Ikeda et al. J; Nutr. Sci. Vitaminol., 27, 243, 1981. They add, to the rabbits' food, cholesterol and sitosterol or sito-stanol (at the dose of 0.5% and 0.2%). Sitostanol inhibits the rise in plasma cholesterol content better than sitosterol. The authors conclude that the hypocholesterolaemic activity of sitostanol results from the inhibiting effect of the absorption of cholesterol by the intestine.

No treatment at present exists for correcting hyperinsulinism and its metabolic consequences, except for a Mediterranean type diet and regular muscular physical activity.

Furthermore, diabetes is controlled or contained by products which regulate glycaemia:

exogenous insulin, sulphamides and/or biguanides, products reducing the absorption of carbohydrates, and aldose reductase inhibitors, not yet on the market.

None of these treatments really treats the causes of diabetes, nor do they cause a truly long-term remission, nor a cure which persists after stopping the treatment.

The treatment of dyslipidaemia is at present based on two types of treatment:

the fibrates: they moderately reduce the cholesterol concentration, and more significantly hypertriglyceridaemia;

the statins (HMG CoA reductase inhibitors): they reduce hypercholesterolaemia and have no action on triglycerides.

These two types of treatment of hypercholesterolaemia and of hypertriglyceridaemia are employed more and more since it is now considered that a reduction of 10% in the level of cholesterol results in a reduction of 20% in the risk of heart disease; they are very often poorly tolerated by patients in which they cause painful effects on the muscles.

Various patents have described different associations, in particular in the form of organometallic complexes which can be used for the treatment and/or prevention of hyperglycaemia, of diabetes and of associated conditions.

French patents FR 2 654 620 and FR 2 676 738 which describe organic derivatives of transition metals, of porphyrin structure;

French patent FR 2 659 333 which describes derivatives of phospholipid structure;

French patent FR 2 686 600 which describes organometallic complexes of inositol, or of its derivatives;

French patent FR 2 686 511, which describes some complexes of aminoacids;

French patent FR 2 686 512, which describes some organometallic complexes with catechol derivatives;

French patent FR 2 686 514, which describes some organometallic complexes in which the ligand contains a cyclic structure containing at least two nitrogen atoms;

French patent FR 2 686 603, which describes some organometallic complexes with dithiocarbamic acid derivatives; and French patent FR 2 686 515 which is more particularly directed towards the use of organometallic derivatives of niobium for the treatment and prevention of disorders in the metabolism of glucides and/or lipids, are cited.

Furthermore, the French patent application FR 2 695 390 describes pharmaceutical compositions containing complexes of tannins with various metals.

SUMMARY OF THE INVENTION

In pursuing their fundamental research in order to elucidate the active plant fractions or complexes of these fractions with metals, the Applicant discovered, entirely by chance, that certain products, fractions or complexes normally inactive or insufficiently active as hypoglycaemiant agents had their activity considerably increased when administered in solution in olive oil. This led the Applicant to seek amongst the many constituents of olive oil those which might result on admixture or by reaction with the products being tested, in more active products.

It is in this way that the Applicant was able to identify novel products composed of organometallic complexes, and obtained by reaction between a derivative of vanadium in oxidation state 4 or 5, and two organic compounds originating from plant extracts, and constituted respectively of sitosterol and acylglycerols.

These products are described in the International Patent Application filed under the number 96 00 153 which describes organometallic complexes obtainable by reaction:

of a cation of a metal (M) in an oxidation state at least equal to 2 useful as a biocatalyst in living metabolism, of free beta or gamma sitosterol, or a mixture of these two products, or of a plant extract containing same, of a mono-, di-, or triglyceride corresponding to formula (I):

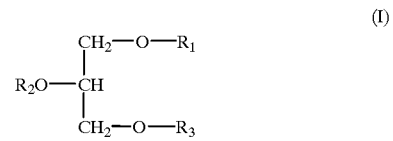

in which:

$R_1$ is an acyl residue of a saturated or unsaturated $C_{14}$–$C_{24}$ fatty acid, hydrogen, or a mono-, di-, or trigalactose or glucose;

$R_2$ is an acyl residue of a $C_{18}$ fatty acid having one unsaturated bond, preferably an oleic acid residue, or one of its positional isomers with respect to the double bond (cis-6,7,9,11 and 13) or one of its iso-branched isomers, $R_3$ is an acyl residue of a saturated or unsaturated $C_{14}$ to $C_{24}$ fatty acid, or a hydrogen atom.

The products described in this document effect a long lasting correction of diabetes in animals, and this with whatever type of animal diabetes, of chemical as well as of genetic origin. These same products correct hyperinsulinism and insulin-resistance in an animal model similar to the <<essential>> arterial hypertension in man, with a simultaneous correction of hyperinsulinism and arterial hypertension.

Analogous complexes can be prepared from other derivatives of metals in which the metal is in an oxidation state of at the least 2, and known for their antidiabetic activity.

Analogous complexes may similarly be formed between the two types of organic derivative described above and various metal cations known to be cations with a biocatalytic activity, these complexes constituting in all cases particularly effective agents for the transport of cations with biocatalytic activity.

"Cations with biocatalytic activity" is understood as meaning both those having a direct biocatalytic activity, and those capable of substituting for biocatalysts and so modifying certain pathological metabolic pathways. The example of vanadium may be mentioned, which by reason of its similar co-ordination chemistry may substitute for phosphate: thus both acid and alkaline phosphatases are inhibited by vanadyl and vanadate compounds; so too is tyrosine phosphatase which induces a stimulation of the phosphorylation of the tyrosine of the peripheral receptor of insulin as well as of the associated protein kinases.

The Applicant, pursuing his researches in the same field, has now identified a novel family of organometallic complexes based on well-defined diglycerides, which shows a particularly great activity in the same field.

The Applicant has also discovered that commercial sitosterol extracted from soya beans contains about 15 to 20% of sitostanol; thus sitosterol, sitostanol or a mixture of these two compounds (commercial sitosterol, for example) possess this same activity when they enter in the composition of the complexes according to the invention.

DETAILED DESCRIPTION OF THE INVENTION

Thus, according to a first aspect, the invention, according to one of its essential characteristics, relates to novel organometallic complexes obtainable by reaction:

of a cation of a metal (M) in an oxidation state at least equal to 2 useful as a biocatalyst in living metabolism, of sitosterol, of sitostanol or of a mixture of sitosterol and sitostanol, or of a plant extract containing sitosterol, sitostanol or a mixture of sitosterol and sitostanol, of the diglyceride of formula (I):

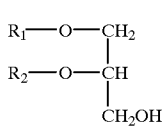

in which:

$R_1$ is an acyl residue of oleic acid ($C_{18}:1$), $R_2$ in an acyl residue of a linear or branched, saturated or unsaturated fatty acid having between 2 and 18 carbon atoms.

According to a preferred variant, $R_2$ is an acetyl or oleoyl group, preferably an acetyl group.

The metal (M) cations which may be used for preparing complexes according to the invention are any cation in an oxidation state of at least 2, and capable of forming complexes with the two types of organic derivative above and known for their catalytic activity in biological systems. In the present paper, biocatalyst will be referred to as designating those metals which display catalytic activity in biological systems.

As examples, if a product is sought with hypolipidaemic activity, or hypoglycaemic and/or anti-diabetic and/or insulinomimetic activity, a metallic derivative of vanadium, niobium, molybdenum, selenium, chromium, or zinc will more particularly be chosen.

In these metal derivatives:

vanadium is advantageously in an oxidation state 3,4 or 5, preferably 4, niobium is advantageously in an oxidation state 4 or 5, preferably 5, selenium is advantageously in an oxidation state 4 or 6, preferably 4, molybdenum is in general in an oxidation state between 4 or 6, preferably 3, chromium is preferably in oxidation state 3, zinc is preferably in oxidation state 2.

By way of examples of metals suitable for other types of application:

antimony or tin, if it is desired to treat auto-immune diseases which affect particularly the nervous system, for example multiple sclerosis (MS), gold in auto-immune pathologies affecting the locomotor system, for example in the case of rheumatoid arthritis, vanadium in neoplasias of the digestive tract, particularly of the pancreas, the colon and the rectum, ruthenium or palladium in respiratory neoplasias, lithium in pathologies of the central nervous system, tin in acquired immuno-deficiency syndromes, may be cited.

By way of examples of metallic derivatives particularly useful according to the invention halides, oxyhalides, sulphates, hydrates, ammonium salts, methoxides of alkali metals or alkaline earth metals which can advantageously be dissolved in water, or sometimes in alcohols, may be cited. Organic derivatives of metals such as acetylacetonates, alkoxides or complexes of metals with organic solvents, for example ethers, THF, and DMF may be mentioned. These organic derivatives of metals are usually soluble in organic solvents, more particularly in chlorinated solvents such as chloroform or dichloromethane.

It will also be possible for the metal to be introduced by previous extraction from foods or plants known to be rich in this metal (black pepper, parsley, basil, dill . . . ).

Sitosterol will preferably be used in admixture with a relative amount of at least 15% of sitostanol. It will be possible for sitosterol and sitostanol to be used pure.

Sitosterol exists commercially, it is however mixed with campesterol and sitostanol. In these commercial products, generally extracted from soya, sitosterol represents 50 to 70% of the product, which is mixed with campesterol and sitostanol in amounts of the order of 15% each respectively.

In a first instance, the activity seemed to be linked exclusively to the presence of sitosterol, since there existed a dose-response relationship between the activity and the amount of sitosterol. Moreover, pure campesterol showed no activity. Continuing its work, the Applicant discovered that the amount of sitostanol present in the mixture varied in the same proportion as the amount of sitosterol. Finally, pure sitostanol showed an activity identical to that of the mixture of sitosterol and sitostanol as previously defined.

Pure sitostanol or stigmastanol is a commercial product obtained by catalytic hydrogenation of sitosterol. Its synthesis from beta-sitosterol was described in 1937: Bernstein, Wallis, J. Org. Chem Soc., 2, 341.

Sitosterol and thus sitostanol can also be prepared by extraction from plants according to the techniques in the literature, for example p. 95 of the thesis presented at Montpellier by Claude Cerdon entitled <<Modulation de la production de sapogénines stéroïdiques en réponse à l'inhibition de la synthèse de stérols>>.

This extraction is carried out advantageously by complexation with metals, according to the method described in particular in French patent FR 2 316 247 in which is described a method for isolating 3-hydroxy-steroids and 3-oxo-steroids from a mixture containing these compounds.

To effect this extraction any plant or product of plant origin known for its relatively high content of sitosterol can be used.

By way of examples of plants or products of plant origin with a relatively high free sitosterol content may be mentioned in particular olive oil, soya bean oil cotton leaves, coffee leaves, wheatgerm, for which the free sterol content and the percentage of sitosterol in the free sterol fraction are given in the table below:

| SPECIES | content/kg | % of sterol fraction |
| --- | --- | --- |
| olive oil | 1310 mg | 91% |
| soya oil | 1908 mg | 53% |
| cotton leaves | 3961 mg | 93% |
| coffee leaves | 9914 mg | 51% |
| wheatgerm | 17336 mg | 67% |

The relative content of sitostanol has not been studied.

It must also be pointed out that the free sterol fraction contains a proportion of the 24 R and 24 S isomers, which are variable according to the plant. This proportion is not well known, since it has been little studied, if at all.

This proportion as well as the relative quantity of sitostanol, which cannot be separated from the sitosterol during purification, could explain the better relative activity of the sterol fraction of some plants, and especially the excess of sitosterol necessary for the preparation of the novel products described in the invention.

A certain number of them, and more particularly those which are found to be the most active in the applications sought after, also exist commercially. This is the case particularly for 1-oleoyl-2-acetylglycerol and for 1,2-dioleoylglycerol, which exist as commercial products with a purity of about 98%. 1-Oleoyl-2-acetylglycerol is, in particular, obtained by chemical or biochemical synthesis, in particular by acetylation in the 2- position by acetyl CoA of 1,2-dioleoylglycerol, or even from a dioleoylphospholipid, in particular phosphatidylcholine which is present in olive oil and is broken down by phospholipase C into a diolein and a phosphorylcholine.

Furthermore, acylglycerols useful for the preparation of the complexes according to the invention can be isolated from the majority of plants.

These acetylglycerols can be extracted from labieae, nettles (*Urtica dioica* and *urens*), sage, bugles, luceme or alfafa (*Medicago sativa*), eucalyptus (*globulus, delegatensis*), *Angelica archangelica* and *Angelica sinensis*, umbelliferous plants, *Gymnema sylvestris* (*asclepiadaceae*), *Marsdenia condurango, Momordica charantia, Gingko biloba*, thistle, green tea, black tea (*Camelia sinensis*), rhubarb, *Dioscorea dumetorum* (*dioscoreaceae*), *Indigofera arrecta* (*papilionaceae*), *pittosporaceae, Agrimonia eupatoria, Curcuma xanthorrhiza* (roxb.), *Uncaria gambier* (roxb.), *Swertia chirayita* (roxb.), *resedaceae* (*Reseda phyteuma, lutea, alba, luteola*), *harpagophytum, rubiaceae, gentianaceae, Asparagus racemosus*, hawthorn (*Crataegus oxyacantha*), mistletoe (*Viscum album*), mangrove (*rhizophoraceae*), kaki, oak (*fagaceae*), bramble, hamamelis (*hamamelidaceae*), ratanhia (*krameriaceae*), salicaria (*lithraceae*), calophyllum (*clusiaceae*), acacias, (*mimosoideae*), quebracho (*anacardiaceae*), grapes(*Vitis vinifera, ampellidaceae*), blackcurrant (*saxifragaceae, Ribes nigrum*), blueberry (*ericaceae*), blackberry (*Rubus fructicosus*), elder, red cabbage, garlic (*Allium sativum*), coriander (*Coriandrum sativum*), juniper (*Juniperus communis*), pine (*abietaceae*), maritime pine, cypress (*Cupressus sempervirens*),hibiscus, rhus (*anacardiaceae*), dycotyledonous plants, ferns, gymnospermus, melianthus, rosaceous plants, roses, *Malva verticillata* (*malvaceae*), strawberry, citrus (*rutaceae*), chestnut (*fragaceae*), bistortous plants, leguminous plants, sophora, lespedeza, polygonaceous plants, buckwheat.

Unsaturated vegetable oils are particularly advantageously used as source of acylglycerols, especially olive oil from the first cold pressing.

As a general rule, an oil containing a high concentration of oleic acid will be chosen as a useful source of acylglycerols according to the invention. Such an oil usually contains a high proportion of acylglycerols useful according to the invention.

As examples of such oils may be quoted:
olive oil, where the content of oleic acid ($C_{18}$:1) is between 60 and 80%, European oils being richer in $C_{18:1}$ than oils from North Africa,
sunflower oil, of the variety known as oleic sunflower hybrid, which contains 83% of $C_{18:1}$, instead of the 16% in normal sunflower oil,
safflower oil of the oleic variety which contains 73 to 80% of $C_{18:1}$, instead of the 10–20% in the linoleic variety,
almond oil containing 64 to 82% of $C_{18:1}$,
hazel nut oil containing 66 to 83% of $C_{18:1}$,
avocado oil for which the $C_{18:1}$ content ranges from 36 to 80%.

The fraction containing acylglycerols useful for the preparation of complexes according to the invention can advantageously be prepared from olive oil in the following way: a preliminary purification of the olive oil is affected by passing it through a short column of silica (10 to 15 cm), putting it under vacuum, and eluting with the aid of an organic solvent such as dichloromethane, or a mixture of cyclohexane and ethyl acetate in the proportion 96/4, or any other eluent with a similar polarity, so as to isolate the triglycerides present in the oil. The silica is then washed with ethyl acetate in order to recover the diglycerides suitable for the invention, as well the monoglycerides fraction and the minor polar components (including phosphatidylcholine).

The fraction thus obtained is then passed down a silica column and eluted with different gradients of ethyl acetate/cyclohexane mixtures ranging between 10/90 and 100/0 so as to separate the different chemical families present in the oil, and to recover the active family sought.

1,2-dioleoylglycerol is obtained after elution from the column of the 1,3-diglycerides.

1-oleoyl-2-acetylglycerol is obtained just before 1-oleoylglycerol and 2-oleoyl glycerol.

The complexes according to the invention are, as has been seen above, easily prepared by simply mixing together the three types of compound described above. This mixture is advantageously effected in an organic solvent such as dichloromethane, ether, ethyl acetate, or ethanol.

The complex can also be prepared directly by using an oil as a solvent, which can subsequently be used as the injection solvent for the active product in the case of the injectable form, or as the excipient for the oral form.

The mixture is kept for some hours at a temperature between 30° and 40° C.; the same result can be obtained by flash exposures to a temperature of the order of 50 to 60° C. for a few minutes.

As far as the proportions of the different constituents are concerned, they can vary over a wide range. Nevertheless by correlating the activity of the products obtained with the proportions of the three types of reagent used, it was possible to determine the following proportions, data given with respect to one mole of metal:
sitosterol and/or sitostanol, more generally the mixture of sitosterol and sitostanol or pure sitostanol are advantageously used in the proportion of 1000 to 10000 mole per mole of metal,
the diglyceride is advantageously used in equimolar proportion with respect to the metal. Even so, these proportions can be such that the diglyceride/metal molar ratio be between 1 and 100.

This ratio also varies with the nature of the diglyceride.

In particular, the diglyceride/metal ratio is advantageously between 1 and 100 in the case where the diglyceride is 1,2-dioleoylglycerol.

In the case where the diglyceride is 1-oleoyl-2-acetylglycerol, the ratio is advantageously chosen to be between 1 and 10.

By way of example, for 50 mg of a mixture of sitosterol and sitostanol (in the proportion of 80/20 such as is obtained after purification of soya), and for an amount of vanadium from 1 to 10 µg (expressed as the metal), 1 to 2 mg of 1,2-dioleoylglycerol or 20 to 500 µg of oleoyl acetyl glycerol will preferably be used.

The different constituents are formally identified by the appropriate analytical methods:

sitosterol and sitostanol by gas phase chromatography, HPLC or $^1$H NMR.

acylglycerol by HPLC, with a light diffusion detector, on a $C_{18}$ kromasil column, with an eluent composed of isocratic acetonitrile.

The mass peak of the complex is not detectable by the usual methods, such as chemical ionisation and electron impact, which may be explained by the fact that the complexes formed by these two constituents with the metal are generally unstable, like the majority of organometallic complexes having biological activity.

It was found that the complex obtained was active with much smaller doses of acylglycerol when in position 2 of the glycerol was a shorter acyl chain, between 2 and 18 carbons, and particularly when an acetyl group is in position 2.

Thus, the same activity can be obtained when the organometallic complex is synthesised with ten to a hundred times less oleoyl acetyl glycerol than dioleoyl glycerol.

Furthermore, for 1-oleoyl-2-acetylglycerol as well as for 1,2-dioleoylglycerol, it is the naturally occurring isomer, the "Sn", which possesses the greater activity.

The biocatalytic metal M is advantageously selected from the following metals: zinc, iron, copper, magnesium, vanadium, titanium, chromium, manganese, cobalt, nickel, gallium, germanium, antimony, tin, indium, palladium, rhodium, ruthenium, technium, molybdenum, niobium, zirconium, yttrium, tantalium, tungsten, rhenium, osmium, iridium, platinium, gold, silver, and thallium.

Particularly advantageously, the metal is vanadium, in oxidation state 3, 4 or 5, preferably 4 or 5, more preferably still 4. This enables an application of the complexes according to the invention as a hypolipidaemic in particular and in the treatment and/or the prevention of diabetes and its complications.

According to another of its aspects, the invention relates to the use of the complexes described above as agents for carrying cations with biological activity, the ligands bound to the metal enabling the bioavailability of the metal to be increased.

Such an application is all the more important because in general, the person skilled in the art knows that the difficulty in the therapeutic utilisation of metallic cations is linked to their toxicity at the active doses: well-known examples are lithium salts used in psychiatric pathology, or platinium, ruthenium, or palladium salts used in the treatment of cancer.

The example of vanadium in the treatment of diabetes and its complications illustrates this problem well, and the solution provided by the present invention. In fact:

vanadium salts, in development for a decade (vanadyl and vanadate) are active in animals at doses of 5 to 10 mg/kg (expressed as metal) introduced peritoneally; at this dose, they are very toxic, and cannot be administered to man.

certain organic complexes described in recent years, notably in European patent No. 0 305 264, filed the 10th Aug. 1988, enable obtaining an activity at doses of the order of 1 to 5 mg/kg (expressed as metal).

the organometallic complexes of vanadium, described according to the invention, themselves show optimum activity (return to a normal level of glycaemia and most often a lasting cure of all the symptoms), with a dose of vanadium (expressed as metal) of the order of 1 µg/kg in animals; that is at doses much lower (5000 times less) and devoid of toxicity, comparable to the amounts in the daily diet (40 to 60 µg per day in man).

The organometallic complexes described in the present invention thus optimise the bioavailability of the metallic cation transported, permitting its therapeutic use with low or no toxicity, which shows a considerable advantage with respect to the state of the art.

According to another of its aspects, the invention also relates to pharmaceutical compositions which contain at least one complex as defined previously, and a pharmaceutically acceptable vehicle, excipient, or carrier.

According to a first variant, the pharmaceutical composition contains a complex as previously defined of a single metal.

According to another variant, the pharmaceutical composition can comprise two complexes as previously defined, of two different metals.

Such a mixture results in some cases in a synergic effect: this is the case in particular when the composition contains a mixture of complexes of vanadium and zinc. In this case, it was possible to observe a synergic effect during the use of a pharmaceutical composition containing a mixture of these two types of complex in the treatment of diabetes in certain animal models.

As pharmaceutically acceptable excipient, vehicle or carrier, any excipient vehicle or carrier well-known to the person skilled in the art may be used. The following can be cited as examples in a non-limiting way: lactose, corn starch, glucose, sucrose, sweetening agents such as maltitol syrup, gum arabic, gelatine, carrhagenans, stearic acid, magnesium stearate, dextrin, maltodextrins, mannitol, talc, fats from natural origin, particularly oils of vegetable origin rich in unsaturated fatty acids and sterols. In particular, if eventually necessary, other additives well-known to the person skilled in the art such as stabilisers, drying agents, binders or pH buffers may be used.

The compositions of the invention can be administered in different ways, via the oral route, with a buccal or digestive absorption, via the mucous membrane, subcutaneous, intramuscular route, or the transdermal route (as a patch or gel).

According to another of its aspects, the invention relates to the use of the complexes of the invention for the preparation of a medicine intended for use as a regulating or stimulating agent of biocatalytic systems, particularly in the treatment or the prevention of deficiencies or dysfunctions (genetic or acquired) of enzymatic systems necessitating the presence of metals in the form of cations as catalyst of biochemical reactions, especially in the treatment or the prevention of metabolic, auto-immune or neoplastic illnesses.

In all these uses, the fact that the bioavailability of the metal itself, known to be a biocatalyst, is enhanced by its complexation, is exploited.

Complexation leads in every case to an enhancement of the catalytic power of the metal which allows obtaining an activity at doses of the metal considerably reduced with respect to the doses commonly used.

According to particularly important variants of the invention, the use of complexes will be cited in which the metal is selected from the group consisting of vanadium, niobium, selenium, chromium and molybdenum for the treatment and/or the prevention of cardiovascular complications due to hypercholesterolaemia and/or hypertriglyceridaemia, to insulin dependent or non-insulin dependent diabetes, and to insulin resistance; these pathologies are in particular arterial hypertension, obstructive coronopathies, (myocardial infarction or angor), of ocular or peripheral microangiopathies, also of android-type obesity which accompanies insulin resistance.

Amongst these complexes, those of vanadium in oxidation state 3, 4 or 5 are preferably selected, more preferably still complexes in which the vanadium is in the oxidation state of 4.

Advantageously, for the preparation of dietary products which contain the complex according to the invention, the vanadium can be introduced by carrying out its extraction with a solvent of natural origin such as a vegetable oil or demineralised water. Black pepper, parsley, basil, dill, certain mushrooms . . . , will be cited as foods rich in vanadium. According to another method, the vanadium can be furnished directly by using ground foodstuff, for example ground black pepper which provides 340 $\mu$g of vanadium per gram of pepper.

The following examples are given solely as illustration of the invention.

EXAMPLES

Example: Preparation of a complex according to the invention a) Preparation of a fraction containing more than 90% of oleoyl acetyl glycerol Olive oil is started with which is pre-purified on a silica column of short length (10 to 15 cm). The elution is done with dichloromethane or a 96/4 mixture of cyclohexane/ethyl acetate, under vacuum. This operation enables removing the triglycerides present in the oil.

The silica is then washed with ethyl acetate and the interesting fraction of the oil is collected. This fraction is then passed over a silica column in eluting with different gradients of mixtures of ethyl acetate/cyclohexane between 10/90 and 100/0. This operation enables separating the different chemical families of the oil and to recover the active fraction sought after which is controlled by HPLC with a light diffusion detector.

The oleoyl acetyl glycerol is recovered before the monoglyceride fraction.

b) Preparation of the complex according to the invention 1 g of a commercial mixture of sitosterol/sitostanol in the proportions of 70/15, the remainder being made up of impurities, campesterol in particular, 1.1 mg of VO(Acac)$_2$, 5 mg of oleoyl acetyl glycerol obtained by purification of olive oil, are dissolved in 15 cc of dichloromethane.

The mixture is heated with stirring for one hour.

The solvent is evaporated and the complex is recovered.

c) Other example of preparation of a complex according to the invention 1 g of commercial sitostanol, 1.1 mg of VO(Acac)$_2$, 5 mg of oleoyl acetyl glycerol obtained by purification of olive oil, are dissolved in 15 cc of dichloromethane.

The mixture is heated several times at 50° C. for a few minutes. The solvent is evaporated and the complex is recovered.

Example 2- Preparation of a complex according to the invention in using a commercial glyceride 1 g of commercial sitostanol, 1.1 mg of VO(Acac)$^2$, 20 mg of commercial 1-2-dioleoyl glycerol, are dissolved in 15 cc of dichloromethane.

The mixture is heated several times at 50° C. for several minutes.

The solvent is evaporated and the complex is recovered.

Example 3: Preparation of a pharmaceutical composition

A pharmaceutical composition is prepared from one of the complexes formed according to Example 1 or 2 in the following way:

The complex is incorporated in the liquid used as excipient or injection solvent, and the solvent is removed with a rotary evaporator for example. The product may then be administered.

The complex may also be incorporated in a patch for transdermal diffusion. The complex can also be in the form of a solid contained in gastro-resistant capsules.

Example 4: Preparation of a complex according to the invention 1 g of commercial sitostanol, 100 $\mu$g of VO(Acac)$_2$, 10 mg of commercial 1-oleoyl-2- acetyl-Sn- glycerol, which is kept at a temperature lower than 0° C. until the moment to carry out the mixture of the components in order to prevent a 1–3 position transposition which has no more activity; are dissolved in 15 cc of dichloromethane.

20 cc of codex soya oil are added; the mixture is kept in stirring it for 30 minutes at 40° C. The solvent is then evaporated; the active product is ready to be injected.

Example 5: Preparation of a pharmaceutical composition according to the invention 15 g of commercial sitostanol; and 1.5 mg of VO(Acac)$_2$;

are dissolved in 150 ml of first cold pressed olive oil (which contains the acylglycerols necessary for preparing the complex according to the invention).

The mixture is kept stirred for an hour at 35° C. No organic solvent other than the oil is used. The product is ready to be absorbed per os.

Example 6: Preparation of a dietary product of medical use 150 ml of first cold pressed olive oil;

1 g of ground black pepper (340 $\mu$g of vanadium);

15 g of commercial sitostanol;

The mixture is kept stirred for an hour at 35° C. No organic solvent other than the oil is used. The complex according to the invention is formed, and the product is ready to be absorbed per os.

Example 7: Pharmacological tests

The complex obtained according to Example 3, from Preparation I b, is evaluated according to the following procedure:

male Wistar strain rats originating from the Iffa-Credo Company and weighing on average 160 g are kept 4 days under observation and receive ad libitum food and drinking water. They are submitted to a temperature of 21° C.±1° C., and to a day/night cycle of 12 hours.

they are then anaesthetised with diethyl ether and a dose of 60 mg/kg of streptozotocin in solution in a citrate buffer at pH 4.5 is administered to them by injection into the penal vein (rat model known as STZ);

three days later, the animals (which weigh about 200 g) possess a glycaemia between 3 and 4.9 g/l are grouped by batch of 6 animals, 3 per cage and are submitted to the treatment by the substance to be tested by intra-peritoneal injection (hereinafter referred to as IP) in solution in a fraction extracted from olive oil and which contains only triglycerides of neutral character with respect to the complexes to be tested.

A batch of rats is also made up which are diabetic controls, which receive the same volume of triglycerides extracted from olive oil, via the IP route. The control of the glycaemia is carried out at the desired time with a Glucometter III AMES (Bayer) on glucofilm, when it is an evaluation test of a hypoglycaemic effect at 2 and 6 hours after the administration, or with a Glucometter I AMES, on glucostix when it is a treatment over several days, which serves at evaluating the regulating role of the glycaemia and an eventual effect remaining after the stopping the treatment.

The taking of a drop of blood during each determination is effected by incision of the tip of the tail.

Table I below gives the results obtained during the treatment of various batches of rats by following the protocol of the preceding paragraph, and in using the product prepared according to Example 3 with the complex described in Example I b. Table I below gives, for 3 lots of 6 diabetic STZ rats, the results obtained on days D0, D4, D8 and D11 of the treatment.

This Table specifies for days D4, D8, D11:
- the level of glycaemia,
- the variation in this level of glycaemia with respect to the level on D0,
- the number of corrected rats; "corrected rats" is understood as meaning those which have a glycaemia lower than 1.50 g/l, and
- the difference in weight compared to D0 (weight).

| D0 | D4 | | | | D8 | | | | D11 | | | |
|---|---|---|---|---|---|---|---|---|---|---|---|---|
| glycaemia | glycaemia | variation | corrected | weight | glycaemia | variation | corrected | weight | glycaemia | variation | corrected | weight |
| 3.17 | 2.12 | 32% | 2 | 2 | 1.43 | 55% | 5 | 11 | 2.05 | 35% | 4 | 25 |
| 3.23 | 1.85 | 43% | 4 | −2 | 1.77 | 45% | 4 | 14 | 1.70 | 47% | 4 | 23 |
| 3.48 | 2.31 | 34% | 2 | −5 | 1.69 | 51% | 4 | 14 | 1.89 | 46% | 4 | 28 |

Table II below gives the results obtained for 1 batch of 6 diabetic STZ rats, in following the same protocol as before in using the product as described in Example 3, in using the complex prepared in Example 1 c.

| D0 | D4 | | | | D8 | | | | D11 | | | |
|---|---|---|---|---|---|---|---|---|---|---|---|---|
| glycaemia | glycaemia | variation | corrected | weight | glycaemia | variation | corrected | weight | glycaemia | variation | corrected | weight |
| 3.73 | 2.47 | 34% | 1 | 19 | 2.42 | 35% | 2 | 37 | 2.33 | 38% | 4 | 54 |

Example 8: Clinical test

A clinical study was carried out on 10 ill subjects having a dyslipidaemia, 7 men and 3 women. The average age was 61 years old. The treatment was established for a period of time of 30 days; a lipid determination was carried out before the treatment and at the end of treatment.

The product given is that described in Example 5 at the dose of 5 ml per day, which corresponds to a dose of vanadium expressed as the metal of 10 μg per day.

No modification of the diet was made. The results are described in Table 3 below:

| | | | CHOLESTEROL lower than 2.40 g/l | | TOTAL CHOLESTEROL/HDL lower than 4 | | TRIGLYCERIDES 0.50 to 1.50 g/l | |
|---|---|---|---|---|---|---|---|---|
| NORMAL VALUE | | | before | after | before | after | before | after |
| | NAME | AGE | treatment | treatment | treatment | treatment | treatment | treatment |
| 1 | LEG. | 46 | 2.67 | 2.47 | 5.28 | 3.32 | 2.64 | 0.92 |
| 2 | REN. | 74 | 2.94 | 2.30 | 5.15 | 4.34 | 2.10 | 1.50 |
| 3 | NOU. | 66 | 3.51 | 2.43 | 3.69 | 2.47 | 1.07 | 0.65 |

-continued

|   |      |    |      |      |      |      |      |      |
|---|------|----|------|------|------|------|------|------|
| 4 | CAR. | 69 | 2.91 | 2.77 | 4.16 | 4.26 | 2.11 | 1.75 |
| 5 | LET. | 74 | 2.71 | 2.85 | NR   | NR   | 1.89 | 2.65 |
| 6 | DUF. | 48 | 1.97 | 2.28 | 6.15 | 5.56 | 1.57 | 2.01 |
| 7 | MAR. | 62 | 3.04 | 2.18 | NR   | NR   | 2.19 | 1.33 |
| 8 | KOH. | 48 | 2.90 | 1.98 | 6.30 | NR   | 0.94 | 0.73 |
| 9 | CAR. | 64 | 3.25 | 3.25 | NR   | NR   | 0.81 | 0.51 |
| 10| ALB. | 64 | 3.20 | 3.00 | 4.10 | 3.70 | 0.69 | 0.63 |
|   | Average | 61 | 2.91 | 2.56 | 4.98 | 3.94 | 1.60 | 1.27 |

Analysis of the results:

| | Difference before/after treatment | | |
|---|---|---|---|
| | Cholesterol | Cholesterol/HDL | Triglycerides |
| Average | −0.35 | −0.81 | −0.33 |
| Variance | 0.24 | 0.51 | 0.46 |

The calculations on the averages show an increase in the three variables (cholesterol, total cholesterol/HDL, and triglycerides).

A significant difference is demonstrated for:

total cholesterol/HDL variable with an error risk ax of 5% with a degree of chance of 0.02, the cholesterol variable with an error risk a of 5% with a degree of significance than 0.03, the triglyceride variable, although well increased, is not significant with this amount of cases; the number of cases estimated necessary for a significant result is 13 patients.

The hypolipidaemic activity demonstrated is not in exhaustive relation with:

the cholesterol: in fact by comparison with the publication describing the hypocholesterolaemic activity of cholesterol in man (and by analogy in the rabbit) a moderate activity was demonstrated with a daily dose of 0.2 g of sitostanol for one year.

However, during these studies, the provision of sitostanol is 500 mg per day, and the activity is demonstrated after 20 days of treatment, olive oil: in fact, in the dietary intervention study in Lyons (Prof. Serge Renaud) in which were included 600 patients having had, in the previous six weeks, a myocardial infarction and randomised in two groups; the treated group received dietary orders replacing butter and animal fats with olive oil. After a screen of on average 27 months, it appears that the treated group had a cardiovascular mortality reduced by 70%, but no difference in the lipid parameters; the consumption of olive oil had not lowered the cholesterol levels.

The results are well in relation with the organometallic complex according to the invention.

What is claimed is:

1. Organometallic complex which is a reaction product of:

a cation of a metal (M) in an oxidation state at least equal to 2 useful as a biocatalyst, sitosterol, sitostanol, a plant extract containing sitosterol, a plant extract containing sitostanol, a plant extract containing a mixture of sitosterol and sitostanol or a mixture thereof, and a diglyceride of formula (I):

$$R_1\text{—O—CH} \atop R_2\text{—O—CH} \atop \text{CH}_2\text{OH} \qquad (I)$$

in which:

R$_1$ is an acyl residue of oleic acid C$_{18}$:1),

R$_2$ in an acyl residue of a linear or branched, saturated or unsaturated acid having between 2 and 18 carbon atoms.

2. Organometallic complex according to claim 1, wherein R$_2$ is an oleic acid residue.

3. Complex according to claim 1, wherein R$_2$ is an acetyl group.

4. Complex according to claim 1, wherein the mixture of sitosterol and sitostanol is obtained from soya.

5. Complex according to claim 1, wherein the sitostanol is obtained by hydrogenation of sitosterol.

6. Complex according to claim 1, wherein the diglyceride is obtained by isolation from olive oil or an oil rich in oleic acid.

7. Complex according to claim 1, wherein the metal is selected from the group consisting of zinc, iron, copper, magnesium, vanadium, titanium, chromium, manganese, cobalt, nickel, gallium, germanium, antimony, tin, indium, palladium, rhodium, ruthenium, technium, molybdenum, niobium, zirconium, yttrium, tantalum, tungsten, rhenium, osmium, iridium, platinum, gold, silver, and thallium.

8. Complex according to claim 1, wherein the metal is vanadium in an oxidation state of 3, 4 or 5.

9. Complex according to claim 1, wherein the metal is obtained by extraction from a plant high in content of the metal, or by use of the plant in a pulverised form.

10. Method of preparation of a complex according to claim 1, comprising forming a mixture to obtain the reaction product in an organic solvent or an oil.

11. Method according to claim 10, wherein said mixture is heated at a temperature between 30° and 40° C. for one to several hours, or heated with a few flash exposures at a temperature of the order of 50° to 60° C. for a time sufficient to obtain said reaction product.

12. Pharmaceutical composition containing at least one complex as defined in claim 1, and a pharmaceutically acceptable excipient.

13. Composition according to claim 12, wherein the complex is a vanadium complex.

14. Composition according to claim 12, wherein said diglyceride is 1-2-dioleoyl glycerol.

15. Composition according to claim 12, wherein said diglyceride is 1-oleoyl-2-acetyl glycerol.

16. Dietary product containing at least one complex as defined in claim 1, in which the diglyceride is provided by olive oils which olive oil also acts has an excipient for the product.

17. Method for improving the bio-availability of metal cation in a mammal, comprising delivering to the mammal said metallic cation in an organometallic complex which is a reaction product of:

a cation of a metal (M) in an oxidation state at least equal to 2 useful as a biocatalyst, sitosterol, sitostanol, a plant extract containing sitosterol, a plant extract containing sitostanol, a plant extract containing a mixture of sitosterol and sitostanol or a mixture thereof, and a diglyceride of formula (I):

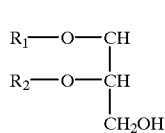

(I)

in which $R_1$ is an acyl residue of oleic acid ($C_{18:1}$), $R_2$ in an acyl residue of a linear or branched, saturated or unsaturated acid having between 2 and 18 carbon atoms.

18. Method according to claim 17, for the treatment or the prevention of genetic or acquired deficiencies or dysfunctions of enzymatic systems necessitating the presence of metals in the form of cations as catalysts of biochemical reactions.

19. Method according to claim 17, for the treatment or prevention of a disease selected from the group consisting of hypercholesterolaemia, hypertriglyceridaemia, insulin-dependent diabetes, non-insulin-dependent diabetes, insulin resistance, cardiovascular diabetic complications, obstructive coronaropathies, ocular or peripheral microangiopathies, peripheral obliterating arteriopathies, and android-type obesity.

20. Method according to claim 17, wherein the metal cation is selected from the group consisting of vanadium, niobium, selenium, chromium, zinc and molybdenum.

21. Method according to claim 20, wherein the metal is vanadium in an oxidation state of 3, 4 or 5.

22. Method according to claim 17, wherein the diglyceride is 1,2-dileoyl glycerol or 1-oleoyl-2-acetyl glycerol.

23. Method according to claim 13, wherein the sterol is a mixture of sitosterol and sitostanol, or pure sitostanol.

24. Method according to claim 13, wherein the mammal is a human and said metallic cation is administered in an amount of about 10 to 60 micrograms per day.

* * * * *

UNITED STATES PATENT AND TRADEMARK OFFICE
CERTIFICATE OF CORRECTION

PATENT NO. : 6,129,924
DATED : October 10, 2000
INVENTOR(S) : Jean-Claude Maurel et al.

It is certified that error appears in the above-identified patent and that said Letters Patent is hereby corrected as shown below:

Title page,
Change "[22] PCT Filed: June 30, 1997" to -- [22] PCT Filed: June 27, 1997 --

Signed and Sealed this

Twentieth Day of November, 2001

Attest:

NICHOLAS P. GODICI
*Attesting Officer*   *Acting Director of the United States Patent and Trademark Office*